(12) United States Patent
Winther et al.

(10) Patent No.: US 6,569,471 B2
(45) Date of Patent: May 27, 2003

(54) METHOD FOR THE TREATMENT OF SYMPTOMS RELATED TO NORMAL HORMONAL VARIATIONS IN WOMEN

(75) Inventors: Kaj Winther, Copenhagen (DK); Christer Hedman, Mölnlycke (SE); Lars Kärnerud, Tenhult (SE)

(73) Assignee: Natumin Pharma AB, Huskvarna (SE)

( * ) Notice: Subject to any disclaimer, the term of this patent is extended or adjusted under 35 U.S.C. 154(b) by 0 days.

(21) Appl. No.: 09/942,967

(22) Filed: Aug. 31, 2001

(65) Prior Publication Data

US 2002/0061337 A1 May 23, 2002

Related U.S. Application Data

(60) Provisional application No. 60/229,308, filed on Sep. 1, 2000.

(51) Int. Cl.⁷ .............................. A61K 35/78
(52) U.S. Cl. ...................... 424/778; 424/725
(58) Field of Search ................. 424/725, 778

(56) References Cited

U.S. PATENT DOCUMENTS 5,569,459 A  10/1996  Shlyankevich

FOREIGN PATENT DOCUMENTS

EP       1 057 483 A     12/2000

OTHER PUBLICATIONS

Dr. Kaj Winther, "Cognitive Function and Natural Medicines", Paper No. 29, from *Vitafoods International Conference 2000*, May 3–5, 2000, Geneva, Switzerland.
K. Winther et al., "P01.24: Pre–Menstrual Tension is Markedly Reduced by Femal, a Natural Product", from *Maturitas: The European Menopause Journal*, Jun. 2000, vol. 35, suppl. 1.
K. Winther et al., "183: Premenstrual Tension (PMS) Symptoms Such as Weight Gain and Raw Lutheal Phase Score are Reduced by Femal, A Natural Product", from *Nordisk Forening For Obstetrikk Og Gynekologi*, Jun. 2000, Oslo.
K. Winther et al., "A Pollen Pistil Extract, Femal, Reduces Weight Gain, Irritability and Dysphoric Disorders in Women Suffering from Premenstrual Syndrome (PMS)", from *Recent Research in Gynecological Endocrinology*, Dec. 2000, pp. 57–61, New York: The Parthenon Publishing Group.
Femal: Natural help for PMS, http://www.sisuhealth.com/products/Femal.html retrived Apr. 24, 2001.
Menopause treatment options (continued), http://www.menopause.org/mgremedies.htm retrived Apr. 24, 2001.

*Primary Examiner*—Jon P. Weber
*Assistant Examiner*—Patricia Patten
(74) *Attorney, Agent, or Firm*—Browdy and Neimark, P.L.L.C.

(57) ABSTRACT

A method for the treatment of symptoms related to normal hormonal variations in women during fertile, peri- and post-menopausal age, by the administering of a composition comprising, as active ingredients, a water and/or fat-soluble cytosolic extract of pollen, optionally combined with Royal Jelly and Vitamin E.

16 Claims, No Drawings

METHOD FOR THE TREATMENT OF SYMPTOMS RELATED TO NORMAL HORMONAL VARIATIONS IN WOMEN

The present application claims the benefit of U.S. Provisional Appln. No. 60/229,308, filed Sep. 1, 2000.

FIELD OF THE INVENTION

The invention relates in a first aspect to a method for the treatment of symptoms related to normal hormonal variations in women during fertile as well as, peri- and post-menopausal age, by the administering of a composition comprising, as active ingredients, a water and/or fat soluble cytosolic extract of pollen, optionally combined with Royal Jelly and Vitamin E.

The invention, in another aspect, relates to the use of a composition comprising, as active ingredients, a water and/or fat soluble extract of pollen optionally combined with Royal Jelly and Vitamin E for the manufacturing of a medicament for the treatment of symptoms relating to normal hormonal variations in women during fertile, as well as peri- and post-menopausal age.

BACKGROUND OF INVENTION

An extract of combined pollen and pistils combined with a pollen grain extract, Royal Jelly and Vitamin E has been sold by Interhealth AB, Kungsangsvagen 27, 561 56 Huskvarna, Sweden, for the treatment of Pre-Menstrual Syndrome (PMS).

SUMMARY OF INVENTION

Said composition was thought to be active against PMS symptoms in general but the present inventors during research work found out that the composition as disclosed in the application showed an unexpected advantageous effect on some symptoms relating to normal variations in the hormone cycle of women. Other symptoms, such as heart rate and blood pressure, remain unaffected of the remedy.

However, unexpected is an beneficial effect on some symptoms relating to normal hormone variations of women of fertile, as well as peri- and post-menopausal age, obtained by the administering of a composition comprising, as active ingredients a water- and/or fat-soluble cytosolic extract of pollen and/or pistils, optionally in combination with Royal Jelly and Vitamin E.

Said symptoms in the peri- and post-menopausal women are selected from menopausal hot flashes, tendencies of sweating, palpitations, muscle pains, headache, difficulties in passing water, stress incontinence, dysphoria, dry vaginal and mucous membranes, arthralgia, water retention, irritability, and variations in mood.

For women in fertile age the most unexpected and surprising effects were obtained on the symptoms selected from irritability, dysphoria, bloatness, edema, breast tension (mastalgia), weight changes, tension, headache, sleep disturbances, overall wellbeing and interference in social and professional life.

The active composition comprises cytosolic extracts of combined pollen and pistils (PI 82), and a pollen extract (GC FEM) and optionally, as excipients, Royal Jelly and Vitamin LE.

A daily dosage should contain from 60 to 960 mg, preferably 120 mg of PI 82, and from 18 to 288 mg, preferably 36 mg, of GC FEM and from 3 to 48 mg, preferably 6 mg, of Royal Jelly. Vitamin E might be included in an amount of from 5 to 80 mg, preferably 10 mg. The composition can be administered in any suitable form and can, given as a tablet be administered to the woman in need thereof, 1 to 8 times daily.

Preferably, a daily dosage should give from 60 to 480 of PI 82, and from 20 to 140 of GC FEM and from 2 to 30 of Royal Jelly. Vitamin E might be supplied in an amount from 5 to 60 mg/day supplied 1 to 6 times daily.

More preferably, the ingredients are included in the remedy in amounts ranging from 60 to 360 mg of PI 82, 20 to 70 mg of GC REM and 2 to 15 mg of Royal Jelly, and 10 to 40 mg of Vitamin E, supplied 1 to 4 times/day.

Most preferably, the ingredients are included in the remedy in an amount of 120 mg PI 82, 36 of GC FEM, 6 mg of Royal Jelly and 10 mg of Vitamin E, supplied 1 to 4 times/day.

The remedy comprising the active ingredients should be submitted to the women in need thereof during at least one month, preferably at least two months.

Other excipients are included in amounts well known to any one skilled in the art of pharmaceutical sciences.

The cytosolic pollen-pistil extract, PI 82, contains mimics of the antioxidant enzyme super-oxide dismutase (SOD), the cytosolic extract, GC FEM, contains natural bioflavonoides, vitamins, enzymes and trace elements. Royal Jelly is rich in pantothenic acid (also called Vitamin $B_5$), further vitamins and sterols. Royal Jelly is preferably used in lyophilized form. The pollen and pistils used for the natural extracts are selected and harvested primarily from selected members of the grass (Poaceae) family. They have been specially treated to minimize any risk of allergic pollen reactions. The products can be purchased from Natumin Pharma AB, Kungsängsvägen 27, S-561 51, Huskvarna, Sweden, the Royal Jelly from AB Montoil, Box 24150, S-104 51 Stockholm, Sweden. Vitamin E is preferably used in the form, Dry Vitamin E 50%, Type SD, from F. Hoffmann-La Roche Ltd., CH-4070 Basel, Switzerland. In the preparation dl-alfa-tokoferol is used but other forms might also be valuable.

Disorders relating to normal variation of the sex hormone cycle of women of fertile age are tension, irritability, dysphoria, abdominal distension or bloatness, severe mastalgia (breast tension), headache or migraine, edema, weight changes and sleep disturbances. The overall well being as well as the social and professional life may be influenced.

Over the years at least different treatment options have been suggested to be effective for the treatment of the above-mentioned symptoms. However few have shown a consistent efficacy on irritability, dysphoria, bloatness and edema, tension, breast tension, weight gain, headache and sleep disturbances related to normal variations in the sex hormone cycle of women of fertile age. The pharmacological treatments that have been tried include serotonin re-uptake inhibitors, diuretics, hormonal treatment as well as dietary interventions with e.g. vitamin and mineral supplementation, and natural products. Many of the compounds used for the treatment are limited due to adverse effects. Therefore it is a great need for safe compounds with a consistent efficacy.

DETAILED DESCRIPTION OF THE INVENTION

The active composition in the invention is a new remedy with the aim to be beneficial for the treatment of symptoms related to variations in the normal sex hormone pattern, such as the above mentioned. It is a combination of natural health products and comprises a cytosolic pollen-pistil extract (PI 82), a cytosolic pollen grain extract (GC FEM), and optionally Royal Jelly, a substance produced by worker honey bees, Vitamin E Further, common drug processing compounds may be included such as diluents, glidants, lubricants, disintegrants, flavoring and coloring agents well known to the man skilled in the art of pharmaceutical sciences. The active ingredients can be included in formulations of any form, such as tablets, powders, granules, and tinctures or included in foodstuff of different origin, e.g. as functional food.

PI 82 is a cytosolic pollen-pistil extract rich in superoxide dismutase (SOD) mimics. The source of PI 82 is freshly harvested pollen grains and pistils. The pollen and pistils are allowed to react under very specific conditions. Substances obtained in this reaction are SOD mimics, flavanoids, tannins and polyphenols. In vitro studies have shown that the extract has high superoxide dismutase activity and prevents the formation of free radicals Experiences from double blind patient investigation show that PI 82 protects the body from free radicals and their negative influence on the body. Furthermore PI 82 improves the red cell function, thus improving oxygen perfusion to different tissues.

GC FEM is another water-soluble cytosolic extract from pollen. The cytoplasm content of the pollen contains in addition to the above-mentioned substances high amount of carbohydrates and protein. Amongst the proteins carotenoids and flavanoids are found. It also contains traces of estrogen substances.

The PI82 and GC FEM extracts are selected and harvested primarily from Poaceae. The extracts are treated to achieve germinal openings of the pollen as well as to minimize risk for allergic pollen reactions.

Royal Jelly is produced by the salivary glands of the worker honeybees from various plant materials. It contains a rich source of e.g. pantothenic acid, which has been called an anti-stress vitamin. It is preferably included in the composition in lyophilized form.

Test of the Effects on Symptoms Relating to Normal Variations of the Sex Hormone Pattern of Women of Fertile Age A double-blind study was performed to investigate the efficacy and tolerability of the active composition in comparison to placebo in outpatients suffering from symptoms relating to normal variations in the sex hormone pattern of women. Patients with depression and anxiety were excluded.

The trial was performed on 29 women aged 27 to 54 years (mean 39.4 years), with regular menstrual cycles of 24 to 34 days. Criteria for admission were women aged 20 to 54 years with regular menses complaining of symptoms related to variations in the normal sex hormone pattern.

After a pre-study screening, half of the patients (Group A) took 2 placebo tablets twice daily, starting on the first day after menstruation and continued this treatment for two menstrual cycles, i.e. treatment period 1. The other half (Group 13) followed the same regimen, but they were administered 2 tablets twice daily each tablet comprising 120 mg PI 82, 36 mg GC FEM, 6 mg Royal Jelly and 10 mg Vitamin B. Thereafter, and without any "wash-out" period, each group crossed over to the other medication for another two menstrual cycles, i.e. treatment period 2. Both groups started their medication periods at the same time. No formal rules for withdrawal, other that the patient's own wish to withdraw, were considered necessary. No dropouts due to protocol deviations were recorded.

Statistical Analysis

A non-parametric method (Wilcoxon signed-rank, matched pair analysis) was used for analysis of differences between treatment scores, on an intention to treat basis. A p-value of 0.05 or less was adopted as the acceptable significance level. All numerical values have been reduced to 3 significant figures. With 29 patients available for evaluation, a day-to-day variation of 12%, a Type I error risk of 5%, and a Type II error risk of 10%, it would be possible to detect a score difference of 16%. To detect a possible "carry-over" effect it was decided that a separate statistical analysis of Group A and B should also be performed (cf. Table 13 and 14). An independent institution outside the clinic performed the statistical analysis.

Drug Formulations, Randomization and Blinding

The active composition and placebo tablets were formulated and packed to be indistiguishable for patients as well as for doctor and nurse. Treatments were allotted at random by computer generation for clusters of four individuals. The code list was generated and kept outside the clinic until the study had been completed. Drug formulations were packed and labeled for one month's treatment, and with a code number identifying the patient.

Results

Effects were analyzed as differences in scores for placebo and treatment with the disclosed composition, respectively.

Of the symptoms from the first test protocol, evaluated with VAS (visual analog scale) by patients, the product significantly reduced four as compared to placebo, viz. irritability ($p<0.05$), dysphoria ($p<0.02$), feeling of being bloated ($p<0.05$), and edema ($p<0.02$). The reduction in scores amounted to 39%, 36%, 41%, and 53% respectively. The reduced awareness of edema agrees well with the 57% reduction in gain in body weight. Tendencies of effects are also shown for mastalgia and headache. The letters "ns" below means "not significant". A spillover effect might be obtained from the treatment with the active compound to the placebo test. According to later follow-up tests, reported in Table 13 and 14, remarkably good effects were obtained.

The scope of the invention is as defied in the appended claims.

Irritability Score

During the first cycle the irritability score (visual analogue scales 1–10) was 4.2 during placebo treatment as compared to 3.1 during treatment with the active composition. The corresponding figures for the second cycle was 4.4 for placebo and 2.8 for the active composition. The difference between placebo and the active composition was statistically significant between the two treatments during the second cycle, while there was a tendency of improvement during the first. The score was statistically significant lower during the second the active composition period compared to the first ($p<0.05$), and a carry-over effect was observed.

TABLE 1

Irritability score (VAS 0–10) during treatment with Placebo and the active composition (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 4.2 | 3.1 | 4.4 | 2.8 |
| Range | 0–9.4 | 0–9.5 | 0–9.3 | 0–9.5 |
| S.D. | 3.3 | 3.0 | 3.4 | 3.1 |
| p-value | ns |  | $p < 0.05$ | |

Dysphoria Score

During the first cycle the dysphoria score (visual analogue scales 1–10) was 3.1 during placebo treatment as compared to 2.6 during the active composition treatment. The corresponding figures for the second cycle was 3.9 for placebo and 2.3 for the active composition. The difference between placebo and the active composition was statistically significant between the two treatments dung the second cycle, while there was a tendency of improvement during the first.

TABLE 2

Dysphoria score (VAS 0–10) during treatment with Placebo and the active composition (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 3.1 | 2.6 | 3.9 | 2.3 |
| Range | 0–7.8 | 0–9.5 | 0–9.2 | 0–9.5 |
| S.D. | 2.7 | 3.1 | 3.1 | 2.9 |
| p-value | ns |  | p < 0.02 |  |

Bloating Score

During the first cycle the bloating score (visual analogue scales 1–10) was 3.9 during placebo treatment as compared to 2.4 during the active composition treatment. The corresponding figures for the second cycle was 3.7 for placebo and 2.2 for the active composition. The difference between placebo and the active composition was statistically significant between the two treatments for the first cycle and on the borderline on the second cycle (0.054). There was a significant carry-over effect.

TABLE 3

Bloating score (VAS 0–10) during treatment with Placebo and the active composition (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 3.9 | 2.4 | 3.7 | 2.2 |
| Range | 0–9.5 | 0–9.5 | 0-9.5 | 0-9.5 |
| S.D. | 3.0 | 2.9 | 3.6 | 2.9 |
| p-value | p < 0.05 |  | p = 0.054 |  |

Edema Score

During the first cycle the edema score (visual analogue scales 1–10) was 3.3 during placebo treatment as compared to 2.2 during the active composition treatment. The corresponding figures for the second cycle was 3.2 for placebo and 1.7 for the active composition. The difference between placebo and the active composition was statistically significant between the two treatments during the second cycle. A significant carry-over effect was found.

TABLE 4

Edema score (VAS 0–10) during treatment with Placebo and the active composition (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 3.3 | 2.2 | 3.2 | 1.7 |
| Range | 0–10 | 0–9.5 | 0–10 | 0–9.5 |
| S.D. | 3.4 | 3.1 | 3.6 | 2.7 |
| p-value | ns |  | p < 0.02 |  |

Mastalgia Score

During the first cycle the mastalgia score (visual analogue scales 1–10) was 3.3 during placebo treatment as compared to 2.9 during treatment with the active composition. The corresponding figures for the second cycle was 3.5 for placebo and 2.5 for the active composition. The differences between placebo and the active composition were not statistically significant between the two treatments.

TABLE 5

Mastalgia score (VAS 0–10) during treatment with Placebo and the active composition (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 3.3 | 2.9 | 3.5 | 2.5 |
| Range | 0–10 | 0–10 | 0–10 | 0–8.3 |
| S.D. | 3.4 | 3.2 | 3.8 | 2.9 |
| p-value | ns |  | ns |  |

Weight Increase

During the first cycle the patients weight increase was 1.2 kg during placebo treatment as compared to 1.0 during treatment with the active compound. The corresponding figures for the second cycle was 1.4 for placebo and 0.6 for the active compound. The difference between placebo and the active compound was statistically significant between the two treatments during the second cycle. It was a statistically significant difference between the first the active compound period and the second. A significant carry-over effect was found.

TABLE 6

Weight (kg) increase in connection with PMTS during treatment with Placebo and the active compound (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 1.2 | 1.0 | 1.4 | 0.6 |
| Range | 0–5.5 | 0–3 | 0–5 | 0–3 |
| S.D. | 1.3 | 1.0 | 1.3 | 0.8 |
| p-value | ns |  | p < 0.01 |  |

Tension Score

During the first cycle the tension score (visual analogue scales 1–10) was 3.4 during placebo treatment as compared to 2.6 during treatment with the active compound. The corresponding figures for the second cycle was 3.7 for placebo and 2.5 for the active compound. The difference between placebo and the active compound was not statistically significant between the two treatments during any of the cycles, even if it was a strong tendency of improvement during the second (p=0.060). There was a statistically significant carry-over effect between the periods.

TABLE 7

Tension score (VAS 0–10) during treatment with Placebo and the active compound (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 3.4 | 2.6 | 3.7 | 2.5 |
| Range | 0–8.2 | 0–9.5 | 0–9.2 | 0–9.5 |
| S.D. | 2.7 | 3.2 | 3.0 | 3.0 |
| p-value | ns |  | ns |  |

Headache Score

During the first cycle the headache score (visual analogue scales 1–10) was 3.7 during placebo treatment as compared to 2.1 during treatment with the active composition. The corresponding figures for the second cycle was 3.0 for placebo and 2.4 for the active composition. The differences between placebo and the active composition were not statistically significant between the two treatments.

TABLE 8

Headache score (VAS 0–10) during treatment with Placebo and the active composition (n = 29) at each menstrual cycle.

|         | Placebo 1st Cycle | Active 1st Cycle | Placebo 2nd Cycle | Active 2nd Cycle |
|---------|-------------------|------------------|-------------------|------------------|
| Mean    | 3.7               | 2.1              | 3.0               | 2.4              |
| Range   | 0–10              | 0–8.9            | 0–9.5             | 0–9.5            |
| S.D.    | 3.3               | 2.8              | 3.4               | 3.1              |
| p-value | ns                |                  | ns                |                  |

Sleep Disturbances Score

During the first cycle the sleep disturbances score (visual analogue scales 1–10) was 2.8 during placebo treatment as compared to 2.0 during treatment with the active composition. The corresponding figures for the second cycle was 3.1 for placebo and 2.5 for the active composition. The differences between placebo and the active composition were not statistically significant between the two treatments.

TABLE 9

Sleep disturbances score (VAS 0–10) during treatment with Placebo and the active composition (n = 29) at each menstrual cycle.

|         | Placebo 1st Cycle | Active 1st Cycle | Placebo 2nd Cycle | Active 2nd Cycle |
|---------|-------------------|------------------|-------------------|------------------|
| Mean    | 2.8               | 2.0              | 3.1               | 2.5              |
| Range   | 0–10              | 0–8.7            | 0–10              | 0–9.3            |
| S.D.    | 3.3               | 3.1              | 3.6               | 3.3              |
| p-value | ns                |                  | ns                |                  |

Safety, Heart Rate

No statistically significant differences between placebo and the active composition were found between the two treatments.

TABLE 10

Heart rate after treatment with Placebo and the active composition (n = 29) after each menstrual cycle.

|         | Placebo 1st Cycle | Active 1st Cycle | Placebo 2nd Cycle | Active 2nd Cycle |
|---------|-------------------|------------------|-------------------|------------------|
| Mean    | 74.2              | 76.3             | 75.4              | 77.6             |
| Range   | 64–90             | 64–94            | 56–88             | 68–92            |
| S.D.    | 6.7               | 8.5              | 8.1               | 6.5              |
| p-value | ns                |                  | ns                |                  |

Systolic Blood Pressure

No statistically significant differences between placebo and the active composition were found between the two treatments.

TABLE 11

Systolic blood pressure after treatment with Placebo and the active composition (n = 29) after each menstrual cycle.

|         | Placebo 1st Cycle | Active 1st Cycle | Placebo 2nd Cycle | Active 2nd Cycle |
|---------|-------------------|------------------|-------------------|------------------|
| Mean    | 114.5             | 114.8            | 112.1             | 113.5            |
| Range   | 90–135            | 90–150           | 95–125            | 90–130           |
| S.D.    | 12.0              | 13.9             | 8.5               | 10.4             |
| p-value | ns                |                  | ns                |                  |

Diastolic Blood Pressure

No statistically significant differences between placebo and the active composition were found between the two treatments.

TABLE 12

Diastolic blood pressure after treatment with Placebo and the active composition (n = 29) after each menstrual cycle.

|         | Placebo 1st Cycle | Active 1st Cycle | Placebo 2nd Cycle | Active 2nd Cycle |
|---------|-------------------|------------------|-------------------|------------------|
| Mean    | 77.4              | 77.1             | 78.1              | 79.4             |
| Range   | 60–90             | 60–85            | 70–90             | 70–90            |
| S.D.    | 6.4               | 7.0              | 5.3               | 5.9              |
| p-value | ns                |                  | ns                |                  |

A further statistical analyze is given in Table 13. The analyze was performed in line with the test of Wilcoxon test performed above. However, the participants obtained placebo during the first two treatment periods and the active composition during the two second treatment periods. The treatment with the active composition shows an unexpected and remarkably better effect as compared to the placebo treatment.

TABLE 13

Group A

| | Mentrual cycle number | | | | | | | |
|---|---|---|---|---|---|---|---|---|
| | 1 | 2 | 3 | 4 | | | | |
| | | | Treatment | | | | | |
| | Placebo | Placebo | Active Femal Code | Active Femal | | P value matrix | | |
| | AP1 | AP2 | AF1 | AF2 | AP1 vs AP2 | AP2 vs AF1 | AF1 vs AF2 | AP2 vs AF2 |
| Tension | 4.1+/−2.9 | 4.2+/−3.3 | 1.7+/−2.8 | 1.2+/−2.4 | ns | 0.0134 | 0.0117 | 0.0012 |
| Irritability | 4.9+/−3.5 | 4.7+/−3.8 | 2.1+/−2.5 | 1.4+/−2.5 | ns | 0.0261 | 0.0020 | 0.0081 |
| Dysphoria | 3.2+/−2.4 | 4.7+/−3.1 | 1.6+/−2.7 | 1.4+/−2.3 | ns | 0.0107 | (0.0907) | 0.0024 |
| Weight change (kg) | 1.5+/−1.6 | 1.6+/−1.6 | 0.6+/−0.9 | 0.4+/−0.5 | ns | 0.0239 | ns | 0.0039 |

TABLE 13-continued

Group A

| | Mentrual cycle number | | | | P value matrix | | | |
|---|---|---|---|---|---|---|---|---|
| | 1 | 2 | 3 | 4 | | | | |
| | | | Treatment | | | | | |
| | Placebo | Placebo | Active Femal Code | Active Femal | | | | |
| | AP1 | AP2 | AF1 | AF2 | AP1 vs AP2 | AP2 vs AF1 | AF1 vs AF2 | AP2 vs AF2 |
| Edema | 4.3+/−3.7 | 4.2+/−3.8 | 0.5+/−0.8 | 0.5+/−0.8 | ns | 0.0039 | ns | 0.0010 |
| Swelling (bloating) | 4.7+/−2.3 | 4.4+/−3.6 | 1.2+/−1.2 | 0.9+/−1.6 | ns | 0.0245 | ns | 0.0107 |
| Breast tension | 4.1+/−3.4 | 3.8+/−3.8 | 2.5+/−3.0 | 1.4+/−2.6 | ns | ns | 0.0195 | 0.0105 |
| Headache | 4.0+/−3.6 | 3.5+/−3.7 | 0.9+/−1.2 | 1.6+/−3.0 | ns | 0.0137 | ns | 0.0371 |
| Sleep disturbance | 4.5+/−3.6 | 5.0+/−3.9 | 2.2+/−3.1 | 2.6+/−3.6 | ns | 0.0266 | ns | 0.0081 |
| Overall wellbeing | 3.2+/−1.3 | 3.4+/−1.5 | 1.5+/−1.2 | 1.5+/−1.1 | ns | 0.0048 | ns | 0.0012 |
| Interf. social/prof. life | 3.7+/−2.7 | 3.7+/−3.3 | 1.2+/−1.6 | 0.8+/−1.8 | ns | 0.0093 | (0.0781) | 0.0034 |

TABLE 14

Group B

| | Mentrual cycle number | | | | P value matrix | | | |
|---|---|---|---|---|---|---|---|---|
| | 1 | 2 | 3 | 4 | | | | |
| | | | Treatment | | | | | |
| | Active comp. | Active comp. | Placebo | Placebo | | | | |
| | | | Code | | | | | |
| | BF1 | BF2 | BP1 | BP2 | BF1 vs BF2 | BF2 vs BP1 | BP1 vs BP2 | BF2 vs BF2 |
| Tension | 3.6+/−3.3 | 3.9+/−3.2 | 2.6+/−2.4 | 3.1+/−2.5 | ns | ns | ns | ns |
| Irritability | 4.3+/−3.1 | 4.3+/−3.2 | 3.5+/−2.9 | 4.1+/−2.9 | ns | ns | ns | ns |
| Dysphoria | 3.5+/−3.6 | 3.2+/−3.4 | 2.9+/−3.0 | 3.0+/−2.9 | ns | ns | ns | ns |
| Weight change (kg) | 1.4+/−1.0 | 0.8+/−1.0 | 0.8+/−0.8 | 1.1+/−0,9 | 0.0239 | ns | ns | ns |
| Edema | 4.1+/−3.7 | 2.9+/−3.4 | 2.4+/−2.9 | 2.1+/−3.0 | 0.0176 | ns | ns | ns |
| Swelling (bloating) | 3.7+/−3.4 | 3.6+/−3.6 | 3.1+/−3.1 | 3.1+/−3.6 | ns | ns | ns | ns |
| Breast tension | 3.4+/−3.4 | 3.6+/−3.1 | 2.5+/−3.3 | 3.3+/−4.1 | ns | ns | ns | ns |
| Headache | 3.4+/−3.5 | 3.2+/−3.1 | 3.4+/−3.0 | 2.5+/−3.2 | na | ns | ns | ns |
| Sleep disturbances | 1.8+/−3.5 | 2.4+/−3.2 | 1.0+/−1.7 | 1.0+/−1.5 | ns | ns | ns | 0.0371 |
| Overall wellbeing | 2.8+/−1.4 | 2.8+/−1.4 | 2.6+/−1.4 | 2.6+/−1.4 | ns | ns | ns | ns |
| Interf. social/prof. life | 2.2+/−2.2 | 2.6+/−3.2 | 1.6+/−2.4 | 1.7+/−2.5 | ns | ns | ns | ns |

During placebo no adverse events were reported. During the first cycle of the active composition treatment three patients noted a shortened menstrual cycle and one patient reported dizziness. During the second cycle with the active composition 5 patients reported a shorter menstrual cycle than normal. Apart from these events the patients tolerated the active composition very well. The lack of severe adverse events is also obvious from Tables 10–12 above.

The results from these studies show that the active composition had a strong effect on tension, irritability, dysphoria, weight gain, edema, bloating, mastalgia, headache, sleep disturbances, overall wellbeing and interference in the social and professional life. The active composition was well tolerated by the patients.

It is interesting to note that the effect of the active composition was more pronounced during the second menstrual cycle compared to the first cycle of active treatment. This indicates that the treatment should be continued for at least two cycles before it should be evaluated whether the product works for the individual patient. For one of the ingredients included in the active composition—PI 82—a similar observation has been made regarding the effect on See radical formation. The onset of effect is seen first after a month treatment. Another reason for this may be that the effect of the active composition continues after having been withdrawn. The observed carry-over effect may indicate his. This effect may be one of the reasons why the efficacy of the active composition is not optimal during the first cycle, i.e. it may be that the onset of efficacy for the product is faster than the present data indicate. This is supported by the data from an open pilot study were the effects were as good during the first menstrual cycle as during the second.

The mode of action is with present scientific knowledge not known. As the product contains three different natural constituents, each with a theoretically contributing effect, the combination of these may be a reason for the observed effect. The constituents PI 82 and GC FEM contain SOD mimics such as flavanoids, tannin polyphenols and carotenoids. These SOD mimics have an effect on free radical formation, which may be a factor involved in redistribution of fluids, including edema, seen under stress situation. An improved oxygen perfusion may also be a contributing effect.

Vitamin E is added to the composition as an active ingredient or as an antioxidant and stabilizer for the tablet formulation.

Test of the Effects on Symptoms Relating to Normal Variations of the Sex Hormone Pattern of Women in the Peri- and Post-Menopause Menopause, which is caused by a lowering of the production of FEMale sex hormones at the age around 50, can to many women generates unwanted symptoms such as hot flushes, attacks of sweating, muscle and possibly joint pain, sleep disturbances, dysphoria, nervousness, mood swings, headache, palpitations (enhanced frequency of heart rate), dry mucous membranes and pain during intercourse, urinary disturbances such as stress incontinent, frequent passing water and pain/irritability of the bladder and urethra during the process of passing water etc.

All these symptoms reflect age related changes which hitherto only have been alleviated effectively by the administration of FEMale sex hormones like estrogen and the like. By the administration of the present active composition, previously known only as a remedy to alleviate symptoms related to Pre-Menstrual Syndromes in common, surprisingly and unexpected a new remedy is obtained, which can relieve and cure the symptoms obstructing the normal life of women in the peri- and post-menopause without negative adverse effects.

The menopause starts around the age of 48–55 years. Four out of 5 women have disturbing menopause symptoms for at least one year and 25% of women have menopause symptoms fore more than 5 years. Three out of four women suffer from hot flushes and many women suffer from dysphoria, mood swings, decreased libido etc. Half of all women have severe symptoms and in a population of 5 million inhabitants, 200,000 women will constantly be in the period of life where menopause trouble is disrupting their life.

Test Mode

Ten women with an average age of 50.8 (range from 46 to 55) years were tested for the trial. All of them had been diagnosed to suffer from climacteric disorders. The menstruation had ceased for 5 women while being irregular for 5. None of the women obtained contemporaneous hormone therapy.

Each of the women obtained one tablet comprising the active ingredients in an amount of 120.0 mg PI 82, 36.0 mg GC FEM and 6.0 mg Royal Jelly, twice daily, morning and evening. The treatment did not affect pulse, or systolic or diastolic blood pressure.

All trials related to VAS (visual analogous scales) on symptoms relating to variations in the normal sex hormone pattern of women in the peri- and post-menopause. The women obtained an interrogation formulae and were requested to estate the symptoms disclosed in the formula according to a scale from 1 to 4, wherein a higher value implies a better result. The results of he tests are compiled in the enclosed Table 14. Low values express favorable results. All statistical calculations are Wilcoxon test for matched pairs, if not otherwise stated, VAS scales were performed on menopausal hot flashes, tendencies of sweating, palpitations, sleep disorders, vertigo, muscle pains, headache, difficulties in passing water (pollakuria), stress incontinence, dysphoria, dry-vaginal and mucous membranes, arthralgia, water retention (edema), irritability, and variations in mood.

The impact of active composition on different menopausal symptoms is shown in Table 15. The participating women evaluated their conditions as regards the symptoms disclosed in Table 15.

TABLE 15

The impact of active composition on different menopausal symptoms. Mean value (standard deviation).

| Menopausal symptoms | Without treatment | Treatment of active composition 1 month | Treatment of active composition 2 months |
|---|---|---|---|
| Hot flushes | 3.08 (2.27) | 2.81 (2.03) | 1.33 (2.00)** |
| Sweating tendencies | 3.94 (2.29) | 2.75 (2.37) | 1.73 (2.54) |
| Palpitations | 2.66 (2.74) | 1.88 (1.37) | 1.31 (1.66)# |
| Muscle pain | 3.40 (3.19) | 2.19 (1.42) | 2.08 (2.40)** |
| Headache | 3.77 (2.84) | 2.38 (2.20)*** | 2.53 (1.98)*** |
| Stress incontinence or frequent passing water (pollakiuria) | 1.73 (2.34) | 1.15 (1.44) | 0.72 (0.85)# |
| Dysphoria | 3.41 (2.05) | 2.16 (1.27)* | 1.60 (1.22)** |
| Dry vaginal and mucous membranes an/or pain during intercourse | 3.02 (2.88) | 1.36 (1.31)*** | 1.52 (2.32)*** |
| Joint pain | 3.94 (2.82) | 1.91 (1.03) | 1.48 (1.30)** |
| Mood | 3.05 (2.26) | 2.72 (1.90) | 1.73 (1.15) |
| Edema | 6.04 (2.53) | 4.48 (1.93)* | 3.28 (1.59)** |
| Energy loss | 4.99 (2.15) | 3.82 (1.60)* | 2.72 (2.21)*** |
| Irritability | 3.18 (2.55) | 2.20 (1.78)*** | 1.61 (1.24)* |
| Sleep disturbances | 4.28 (3.89) | 3.00 (3.07) | 2.87 (3.09) |
| Mood swings | 3.33 (2.16) | 2.31 (1.07) | 1.81 (1.63)# |
| Oversensitivity | 4.03 (2.06) | 2.70 (2.07)* | 2.01 (1.79)** |

# = border line significance
\* = p < 0.05
\*\* = p < 0.02
\*\*\* = p < 0.01

Hot flushes: significant (p<0.02) after two months.

Sweating tendencies: significant (p<0.05) after two months

Palpitations: more than 50% reduction (borderline significant).

Muscle pans: significant (p<0.02) after one month and borderline after two months.

Headache: highly significant (p<0.01) after one and two months.

Stress incontinence and/or pollakuria: reduction of about 60%, borderline significant.

Dysphoria: significant after one and two months (p<0.05 and p<0.02).

Dry vaginal or mucous membranes and/or pain during intercourse: significant after one and two months (p<0.01 and p<0.01)>50% reduction.

Joint pain: significant after two months (p<0.02)

Mood: not significant, however a favorable change of about 40% is obvious.

Edema/water retention: reduction of more than 50%, significant after one and two months (p<0.05 and p<0.02).

Energy loss: marked enhancement, significant after one and two months (p<0.05 and p<0.01).

Irritability: reduced by 50% (p<0.01 and p<0.05).

Sleep disturbances show a tendency of effect but is not significant.

Mood swings: borderline significant after two months.

Oversensitivity: significant better after one and two months (p<0.05 and p<0.02).

If all 19 VAS scores were added to a common "over all well being score" a clearly positive effect is shown for 8 of 10 participants, only two were unchanged. Thus, the improvement is significant (p<0.02).

At a direct inquiry of all ten participants whether they have had any advantages or use of the treatment, 6 of them clearly said, "yes" while four answered "don't know" (p<0.05, Chi square).

Below is given an Example of a tablet used according to the invention.

| Active ingredients: | |
|---|---|
| PI 82 (pollen pistil extract) | 120.0 mg |
| GC FEM (pollen extract) | 36.0 mg |
| Secondary ingredients: | |
| ROYAL JELLY (freeze dried) | 6.0 mg |
| VITAMIN E 50% | 20.0 mg |
| Other ingredients: | |
| Mikrocrystallin cellulose | 87.0 mg |
| Dicalciumphosphate | 87.0 mg |
| Magnesium stearate | 4.0 mg |
| Uncoated tablet weight | 360.0 mg |
| Coating: | |
| Shellac | approx. 2.64 mg |
| Talc | approx. 0.36 mg |
| Total weight | approx. 363.0 mg |

What is claimed is:

1. A method for the treatment of symptoms related to normal hormonal variations in women during fertile, peri- and post-menopausal age, by the administration of a composition comprising, as active ingredients, a water and/or fat-soluble cytosolic extract of pollen alone (GC FEM), an extract of pollen and pistils (PI 82), or a combination of said extracts, optionally combined with Royal Jelly and Vitamin E.

2. The method according to claim 1 said composition is a combination of an extract of pollen and pistils (PI 82), and an extract of pollen (GC FEM).

3. The method according to claim 1 wherein the active composition is administered 1 to 8 times per day to a daily dosage of from 60 to 960 mg of PI 82, 18 to 288 mg of GC FEM and optionally 3 to 48 mg of Royal Jelly D.

4. The method according to claim 1 wherein Vitamin B is administered in a daily dosage of from 5 to 80 mg.

5. The method according to claim 1 wherein the active composition is administered 1 to 6 times per day to a daily dosage of from 60 to 480 mg of PI 82, 20 to 140 mg of GC FEM and optionally 2 to 30 mg of Royal Jelly and 10 to 40 mg of Vitamin E.

6. The method according to claim 1 wherein the active composition is administered 1 to 6 times per day to a daily dosage of from 60 to 360 mg of PI 82, 20 to 70 mg of GC FEM and optionally 2 to 15 mg of Royal Jelly and 10 to 40 mg of Vitamin E.

7. The method according to claim 1 wherein the active composition is administered in a daily dosage of 120 mg PI 82, 36 mg of GC FEM, 6 mg of Royal Jelly and 10 mg of Vitamin E.

8. The method according to claim 1, wherein said treatment is for the treatment of one or more of menopausal hot flashes, tendencies of sweating, palpitations, muscle pains, headache, stress incontinence, pollakiuria, dysphoria, dry vaginal and mucous membranes, arthralgia, water retention, irritability, oversensitivity, and variations in mood.

9. The method according to claim 1, wherein said treatment is for the treatment of the symptoms of irritability of women in the fertile phase, wherein said administration is to a women suffering from said symptom.

10. The method according to claim 1, wherein said treatment is for the treatment of the symptoms of dysphoria of women in the fertile phase, wherein said administration is to a women suffering from said symptom.

11. The method according to claim 1, wherein said treatment is for the treatment of the symptoms of bloating of women in the fertile phase, wherein said administration is to a women suffering from said symptom.

12. The method according to claim 1, wherein said treatment is for the treatment of the symptoms of edema of women in the fertile phase, wherein said administration is to a women suffering from said symptom.

13. The method according to claim 1, wherein said treatment is for the treatment of the symptoms of mastalgia of women in the fertile phase, wherein said administration is to a women suffering from said symptom.

14. The method according to claim 1, wherein said treatment is for the treatment of the symptoms of weight gain of women in the fertile phase, wherein said administration is to a women suffering from said symptom.

15. The method according to claim 1, wherein said treatment is for the treatment of the symptoms of tension of women in the fertile phase, wherein said administration is to a women suffering from said symptom.

16. The method according to claim 1, wherein said treatment is for the treatment of the symptoms of headache of women in the fertile phase, wherein said administration is to a women suffering from said symptom.

* * * * *

UNITED STATES PATENT AND TRADEMARK OFFICE
CERTIFICATE OF CORRECTION

PATENT NO.  : 6,569,471 B2
DATED       : May 27, 2003
INVENTOR(S) : Winther et al.

It is certified that error appears in the above-identified patent and that said Letters Patent is hereby corrected as shown below:

Column 13,
Line 1, delete "said composition" and insert therefor -- wherein the water– and/or fat-soluble cytosolic extract --;
Line 1, delete "Vitamin B" and insert therefor -- Vitamin E --;

Column 14,
Lines 16, 21, 25, 29, 33, 37, 41 and 45, delete "women" and insert therefor -- woman --.

Signed and Sealed this

Seventh Day of October, 2003

JAMES E. ROGAN
*Director of the United States Patent and Trademark Office*